(12) United States Patent
Zhou et al.

(10) Patent No.: US 12,076,123 B2
(45) Date of Patent: Sep. 3, 2024

(54) CHEST NON-INVASIVE BLOOD PRESSURE DETECTING PROBE BASED ON PULSE WAVE TRANSIT TIME AND DEVICE THEREOF

(71) Applicant: ZHEJIANG UNIVERSITY, Hangzhou (CN)

(72) Inventors: Congcong Zhou, Hangzhou (CN); Yiming Zhang, Hangzhou (CN); Xuesong Ye, Hangzhou (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 543 days.

(21) Appl. No.: 17/606,305

(22) PCT Filed: Jul. 3, 2020

(86) PCT No.: PCT/CN2020/100155
§ 371 (c)(1),
(2) Date: Oct. 25, 2021

(87) PCT Pub. No.: WO2021/000941
PCT Pub. Date: Jan. 7, 2021

(65) Prior Publication Data
US 2022/0202300 A1 Jun. 30, 2022

(30) Foreign Application Priority Data

Jul. 3, 2019 (CN) .......................... 201910595774.6

(51) Int. Cl.
*A61B 5/021* (2006.01)
*A61B 5/00* (2006.01)
*A61B 5/11* (2006.01)
*A61B 5/265* (2021.01)
(Continued)

(52) U.S. Cl.
CPC ........ *A61B 5/02125* (2013.01); *A61B 5/1102* (2013.01); *A61B 5/265* (2021.01); *A61B 5/266* (2021.01); *A61B 5/28* (2021.01); *A61B 5/6823* (2013.01); *A61B 5/6833* (2013.01); *A61B 2560/0209* (2013.01); *A61B 2562/0219* (2013.01); *A61B 2562/164* (2013.01)

(58) Field of Classification Search
CPC ... A61B 5/02125; A61B 5/1102; A61B 5/265; A61B 5/266; A61B 5/28; A61B 5/6823; A61B 5/6833
See application file for complete search history.

(56) References Cited

U.S. PATENT DOCUMENTS 10,159,417 B2 * 12/2018 Park .................. A61B 5/02125
2014/0236031 A1 * 8/2014 Banet .................. A61B 5/6822
600/513

\* cited by examiner

*Primary Examiner* — William J Levicky
(74) *Attorney, Agent, or Firm* — Muir Patent Law, PLLC (57) ABSTRACT

A chest non-invasive blood pressure detecting probe based on pulse wave transit time and a device thereof are provided. The detecting probe is attached closely to the skin surface of the human chest, and includes a probe body and a patch, which are of split type. The patch is attached and mounted, in a male-female fastener form, on the probe body for use, so that when the patch needs to be replaced, the patch is directly removed and replaced with a new patch, which is convenient for use. The detecting probe is portable and used for continuous dynamic real-time acquiring of the human aortic blood pressure, which is free from the constraints of lead wires, small and comfortable, and high in measuring precision.

16 Claims, 5 Drawing Sheets

(51) Int. Cl.
*A61B 5/266* (2021.01)
*A61B 5/28* (2021.01)

CHEST NON-INVASIVE BLOOD PRESSURE DETECTING PROBE BASED ON PULSE WAVE TRANSIT TIME AND DEVICE THEREOF

CROSS REFERENCE TO RELATED APPLICATION

This patent application is a national phase application of International Patent Application No. PCT/CN2020/100155, filed on Jul. 3, 2020, which claims the benefit and priority of Chinese Patent Application No. 201910595774.6 filed to China National Intellectual Property Administration on Jul. 3, 2019, entitled as "CHEST NON-INVASIVE BLOOD PRESSURE DETECTING PROBE BASED ON PULSE WAVE TRANSIT TIME AND DEVICE THEREOF", the entire content of each of which is incorporated by reference herein.

TECHNICAL FIELD

The present disclosure belongs to the field of non-invasive blood pressure monitoring devices, and particularly relates to a chest non-invasive blood pressure detecting probe based on pulse wave transit time and a device thereof.

BACKGROUND ART

The blood pressure is one of the important physiological parameters reflecting the cardiovascular state of the human. The human blood pressure is fluctuant. Continuous non-invasive blood pressure measurement can detect beat-by-beat arterial blood pressure, which is helpful to the prevention, diagnosis, treatment and control of cardiovascular diseases. At present, non-invasive blood pressure detection technology can be divided into intermittent measurement and continuous measurement. Intermittent measurement methods, which include auscultatory method and oscillometric method, which have the characteristics of high precision. However, the intermittent measurement methods have high requirements for operators and can only obtain intermittent blood pressure values. Continuous measurement methods include arterial tension method, volume compensation method and pulse wave velocity method and so on. Although the arterial tension method and the volume compensation method are mature, they are sensitive to the sensor position, and enable users feel uncomfortable due to venous congestion caused by the long-term measurement. The pulse wave velocity method has become a research hotspot in recent years for its advantages of non-interference and dynamic measurement.

The traditional blood pressure detection method based on pulse wave transit time (PTT) has some problems, e.g., a single blood pressure index is only measured, frequent calibration is needed and the precision is poor. One of the reasons for such problems is as follows: the traditional method ignores the influence of vasoconstriction and vasodilation ability and the PEP (pre-ejection period) on blood pressure fluctuation, and only estimates blood pressure depending on the PTT single parameter, which cannot track ambulatory blood pressure for a long time. In addition, the traditional acquiring sites are usually located in wrist, fingers, limbs, etc. The measured transit time of the pulse wave not only includes the aortic pulse wave transit time linearly related to the blood pressure, but also includes the transit time for the cardiac ejection period, the radial artery or the common carotid artery and the local capillary distal, thereby resulting in errors between the detected blood pressure parameters and the actual blood pressure parameters. Besides, the traditional detecting device is large in size, complex in use, high in sensor rigidity, and easy to cause skin allergy due to colloidal electrodes, thereby causing inconvenience to users.

Therefore, it is necessary to provide a chest non-invasive blood pressure detecting probe which is comfortable to wear, strong in stability and capable of further improving the precision of blood pressure detection. However, due to the need to integrate different detection elements on the wearable probe, new requirements are put forward for the structural design of the probe.

SUMMARY

The purpose of the present disclosure is to provide a chest non-invasive blood pressure detecting probe and device based on pulse wave transit time to solve the problems existing in the prior art.

To achieve the above purpose, the present disclosure provides the following scheme.

A chest non-invasive blood pressure detecting probe based on pulse wave transit time includes a shell, a patch and an elastic component; a bottom of the shell is provided with a flexible bottom plate, and a surface of the flexible bottom plate is provided with a plurality of electrode female fasteners, a photoelectric sensor module and an acceleration sensor; the electrode female fasteners and the acceleration sensor are closely attached on the surface of the flexible bottom plate; the photoelectric sensor module is fixed on the elastic component; the elastic component includes two fixed telescopic rod and a spring conductive wire; the two fixed telescopic rods are fixed at a bottom of the photoelectric sensor module; the flexible bottom plate is provided with slotted holes; the two fixed telescopic rods are inserted into the slotted holes to form a movable pair capable of telescopic adjustment; the bottom of the photoelectric sensor module is connected with one end of the spring conductive wire, and another end of the spring conductive wire is supported on the flexible bottom plate; the photoelectric sensor module protrudes from the surface of the flexible bottom plate without external pressure; a plurality of electrode assemblies are provided in the patch; the electrode assemblies include respective electrode sheets and respective electrode male fasteners; the patch has a same external contour as the surface of the flexible bottom plate, and a middle portion of the patch is provided with a hollow area; the photoelectric sensor module is placed in the hollow area, and the photoelectric sensor module is connected with the flexible bottom plate through the two fixed telescopic rods inserted into the slotted holes; the electrode male fasteners of the electrode assemblies are fixedly embedded on a surface of the patch, the electrode male fasteners and the electrode female fasteners are arranged in one-to-one correspondence, and the electrode male fasteners and the electrode female fasteners are snapped and fixed in pairs; a surface of each of the electrode male fasteners is closely attached with a corresponding one of the electrode sheets.

Preferably, the electrode assemblies are arranged in pairs, the electrode assemblies include two setting manners that are double electrodes and four electrodes; each pair of the electrode assemblies is symmetrically arranged with the photoelectric sensor module as a center.

Preferably, a reference electrode is provided on the patch.

Preferably, the electrode sheets are made of Ag/AgCl, metal or fabric electrodes; a gel layer is coated on a surface of each of the electrode sheets.

Preferably, the photoelectric sensor module includes at least one photoelectric receiving tube and at least one LED array; the at least one photoelectric receiving tube is used for receiving light beams emitted by the at least one LED array and reflected by human skin.

Preferably, a cavity for accommodating a detection circuit is provided between the shell and the flexible bottom plate.

Preferably, the shell and/or the flexible bottom plate are made of polydimethylsiloxane.

A chest non-invasive blood pressure detecting device based on pulse wave transit time includes: an ECG/cardiac impedance signal detector, a pulse signal detector, an acceleration body plethysmography signal detector, a main control/Bluetooth unit, a power supply management unit and a storage unit; the ECG/cardiac impedance signal detector includes an ECG signal AFE (analog-front-end) and the electrode assemblies arranged in pairs above mentioned; the electrode assemblies are electrically connected with the ECG signal AFE; the electrode sheets on the electrode assemblies are used for picking up ECG signals and ICG signals of a human body surface; the ECG signals and the ICG signals are processed and converted by the ECG signal AFE; the pulse signal detector includes a pulse AFE and the photoelectric sensor module above mentioned; the photoelectric sensor module is electrically connected with the pulse AFE; the photoelectric sensor module is configured for picking up human pulse and blood flow volume signals based on a photoplethysmographic method, and the human pulse and blood flow volume signals are processed and converted by the pulse AFE; the acceleration body plethysmography signal detector includes an APG AFE and the acceleration sensor above mentioned is electrically connected with the APG AFE; the acceleration sensor is used for acquiring human arterial acceleration body plethysmography (APG) signals; the APG signals are processed and converted by the APG AFE; the main control/Bluetooth unit includes a main control chip; the main control chip includes a Bluetooth BLE low power-consumption protocol stack, which is electrically connected with the ECG/cardiac impedance signal detector, the pulse signal detector, the acceleration body plethysmography signal detector, the power supply management unit and the storage unit, respectively; the main control chip is used for controlling each signal detection unit to acquire signal data, and performing signal processing on the signal data to obtain a blood pressure result; the signal processing includes signal analysis, feature extraction and blood pressure calculation; the blood pressure result is transmitted to a terminal via the Bluetooth BLE low power-consumption protocol stack; the power supply management unit is used for providing electric energy for each power consumption unit in the detecting device; the storage unit is used for storing local data; the ECG/PPG/APG signal AFE, the main control/Bluetooth unit, the power supply management unit and the storage unit are integrated in the detecting probe.

Preferably, when the electrode assemblies arranged in pairs are used for detecting the ECG signals, one of the electrode assemblies serves as an RA electrode, and another one of the electrode assemblies serves as an LA electrode; when the electrode assemblies arranged in pairs are used for detecting cardiac impedance signals, one of the electrode assemblies serves as a detection electrode, and another one of the electrode assemblies serves as an excitation electrode.

Preferably, the power supply management unit includes a lithium battery module, a voltage stabilizing circuit and a USB interface; the USB interface is used for externally connecting power supply; the lithium battery module is used for internally supplying electric power; and the voltage stabilizing circuit is used for converting a voltage and enabling stable output of the voltage.

According to the specific embodiment provided by the present disclosure, the present disclosure discloses the technical effects as follows. The chest non-invasive blood pressure detecting probe based on pulse wave transit time provided by the present disclosure can be closely attached to the skin surface of the human chest, and includes a probe body and a patch that are split type. The patch is attached and mounted on the probe body for use in the form of a male-female fastener, so that when the patch needs to be replaced, the patch can be directly removed and replaced with a new patch, which is convenient for use. The detecting probe is portable and used for continuous dynamic real-time acquiring of the human aortic blood pressure, which is free from the constraints of lead wires. The detecting probe is small and comfortable, and high in measuring precision, and has higher medical value and broader market application prospects.

In addition, the chest non-invasive blood pressure detecting device based on pulse wave transit time provided by the present disclosure can integrate a signal acquiring system (a ECG signal AFE, a pulse AFE, an APG AFE and a main control/Bluetooth unit) into the above detecting probe, so that the measurement device is simple in structure, convenient to operate, and free from the constraints of traditional measurement airbags for the blood pressure on the human body, and has improved comfort and portability.

BRIEF DESCRIPTION OF THE DRAWINGS

In order to explain the embodiments of the present disclosure or the technical scheme in the prior art more clearly, the drawings needed in the embodiments will be briefly introduced below. Obviously, the drawings in the following description are only some embodiments of the present disclosure. For those skilled in the art, other drawings can be obtained according to these drawings without paying creative labor.

The reference numbers in the figure: shell 1, electrode female fastener 2-1, photoelectric sensor module 2-2, acceleration sensor 2-3, flexible bottom plate 2-4, LED array 3-1, photoelectric receiving tube 3-2, patch 4, electrode male fastener 4-1, gel layer 4-2, first electrode 4-3, second electrode 4-4, reference electrode 4-5, spring conductive wire 4-6, fixed telescopic rod 4-7.

DETAILED DESCRIPTION OF THE EMBODIMENTS

The technical scheme in the embodiments of the present disclosure will be described clearly and completely with reference to the drawings in the embodiments of the present disclosure. Obviously, the described embodiments are only some embodiments of the present disclosure, rather than all the embodiments. Based on the embodiments of the present disclosure, all other embodiments obtained by those skilled in the art without paying creative labor belong to the scope of protection of the present disclosure.

The purpose of the present disclosure is to provide a chest non-invasive blood pressure detecting probe based on pulse wave transit time and a device thereof, so as to avoid the constraints of lead wires. Furthermore, there exists the advantage of small size, high comfort, high measurement precision, higher medical value, wider market application prospect and the like while improving comfort and portability.

In order to make the above objects, features and advantages of the present disclosure more obvious and understandable, the present disclosure will be further explained in detail hereinafter with reference to the drawings and specific embodiments. Technical features of various embodiments of the present disclosure can be combined accordingly without conflicting with each other.

Embodiment 1

As shown in FIGS. 1-10, the chest non-invasive blood pressure detecting probe based on pulse wave transit time provided by the present disclosure includes a shell 1, a patch 4 and an elastic component.

A flexible bottom plate 2-4 is provided at a bottom of the shell 1, and a plurality of electrode female fasteners 2-1, a photoelectric sensor module 2-2 and an acceleration sensor 2-3 are provided on a surface of the flexible bottom plate 2-4.

The electrode female fasteners 2-1 and the acceleration sensor 2-3 are attached closely on the surface of the flexible bottom plate 2-4. The photoelectric sensor module 2-2 is fixed on the elastic component.

The elastic component includes fixed telescopic rods 4-7 and a spring conductive wire 4-6.

Two fixed telescopic rods 4-7 are fixed at a bottom of the photoelectric sensor module 2-2. The flexible bottom plate 2-4 is provided with slotted holes. The two fixed telescopic rods 4-7 are inserted into the slotted holes to form a movable pair capable of telescopic adjustment. The bottom of the photoelectric sensor module 2-2 is connected with one end of the spring conductive wire 4-6, and the other end of the spring conductive wire 4-6 is supported on the flexible bottom plate 2-4. The surface of the photoelectric sensor module 2-2 is higher than the surface of the flexible bottom plate 2-4 without external pressure.

A plurality of electrode assemblies are provided in the patch 4. Each electrode assembly includes an electrode sheet and an electrode male fastener 4-1.

The external contour of the patch 4 is the same as that of the surface of the flexible bottom plate 2-4, and a hollow area is provided in a middle of the patch 4. The photoelectric sensor module 2-2 is placed in the hollow area, and the photoelectric sensor module 2-2 is connected with the flexible bottom plate 2-4 through the fixed telescopic rods 4-7 inserted into the slotted holes. The electrode male fasteners 4-1 of all electrode assemblies are fixedly embedded on a surface of the patch 4. The electrode male fasteners 4-1 and the electrode female fasteners 2-1 are arranged in one-to-one correspondence. The electrode male fasteners 4-1 and the electrode female fasteners 2-1 are snapped and fixed in pairs. The electrode sheet is attached closely to a surface of the electrode male fastener 4-1.

Preferably, the electrode assemblies are arranged in pairs. The electrode assemblies include two setting manners that are double electrodes and four electrodes. Each pair of the electrode assemblies is symmetrically arranged with the photoelectric sensor module 2-2 as a center.

Preferably, the patch 4 is further provided with a reference electrode 4-5.

Preferably, the electrode sheet is made of Ag/AgCl, metal or fabric electrodes. A gel layer 4-2 is coated on a surface of the electrode sheet.

Preferably, the photoelectric sensor module 2-2 includes photoelectric receiving tube(s) 3-2 and LED array(s) 3-1. The photoelectric receiving tube(s) 3-2 may be used for receiving light beams emitted by the LED array(s) 3-1 and then reflected by human skin.

The number of both the photoelectric receiving tube(s) 3-2 and the LED array(s) 3-1 is one or more.

Preferably, a cavity for accommodating a detection circuit is provided between the shell 1 and the flexible bottom plate 2-4.

Preferably, the shell 1 and/or the flexible bottom plate 2-4 are made of polydimethylsiloxane.

The present disclosure further provides a chest non-invasive blood pressure detecting device based on pulse wave transit time. The detecting device includes an ECG/cardiac impedance signal detector, a pulse signal detector, an acceleration body plethysmography signal detector, a main control/Bluetooth unit, a power supply management unit and a storage unit.

The ECG/cardiac impedance signal detector includes an ECG signal AFE and electrode assemblies arranged in pairs in the chest non-invasive blood pressure detecting probe based on pulse wave transit time described above. The electrode assemblies are electrically connected with the ECG signal AFE.

The electrode sheets on the electrode assemblies are used for picking up ECG signals and ICG signals of to human body surface. The ECG signal AFE processes and converts the ECG signals and the ICG signals.

The pulse signal detector includes a pulse AFE and a photoelectric sensor module 2-2 in the chest non-invasive blood pressure detecting probe based on pulse wave transit time described above. The photoelectric sensor module 2-2 is electrically connected with the pulse AFE.

The photoelectric sensor module 2-2 picks up human pulse and blood flow volume signals based on a photoplethysmographic method, and the pulse AFE processes and converts the human pulse and blood flow volume signals.

The acceleration body plethysmography signal detector includes an APG AFE and an acceleration sensor 2-3 of a chest non-invasive blood pressure detecting probe base on pulse wave transit time described above. The acceleration sensor 2-3 is electrically connected with the APG AFE.

The acceleration sensor 2-3 is used for acquiring human arterial acceleration body plethysmography APG signals. The analog front end processes and converts the human arterial acceleration body plethysmography APG signals.

The main control/Bluetooth unit includes a main control chip. The main control chip includes a Bluetooth BLE low power-consumption protocol stack. The main control chip is electrically connected with the ECG/cardiac impedance signal detector, the pulse signal detector, the acceleration body plethysmography signal detector, the power supply management unit and the storage unit, respectively.

The main control chip is used for controlling each signal detection unit to acquire signal data, and performing signal processing on the acquired signals to obtain a blood pressure detection result. The signal processing includes signal analysis, feature extraction and blood pressure calculation.

The blood pressure detection result is transmitted to a terminal via the Bluetooth BLE low power-consumption protocol stack.

The power supply management unit is used for providing electric energy for each power consumption unit in the detecting device.

The storage unit is used for storing local data.

The ECG signal AFE, the pulse AFE, the APG AFE, the main control/Bluetooth unit, the power supply management unit and the storage unit are all integrated in the detecting probe above mentioned.

Preferably, when the paired electrode assemblies are used for detecting ECG signals, one electrode assembly serves as an RA electrode and the other electrode assembly serves as an LA electrode. When the paired electrode assemblies are used for detecting cardiac impedance signals, one electrode assembly serves as a detection electrode and the other electrode serves as an excitation electrode.

Preferably, the power supply management unit includes a lithium battery module, a voltage stabilizing circuit and a USB interface.

The USB interface is used for externally connecting the power supply. The lithium battery module is used for internally supplying electric power. The voltage stabilizing circuit is used for converting a voltage and enabling the stable output of the voltage.

Embodiment 2

Figure 1:
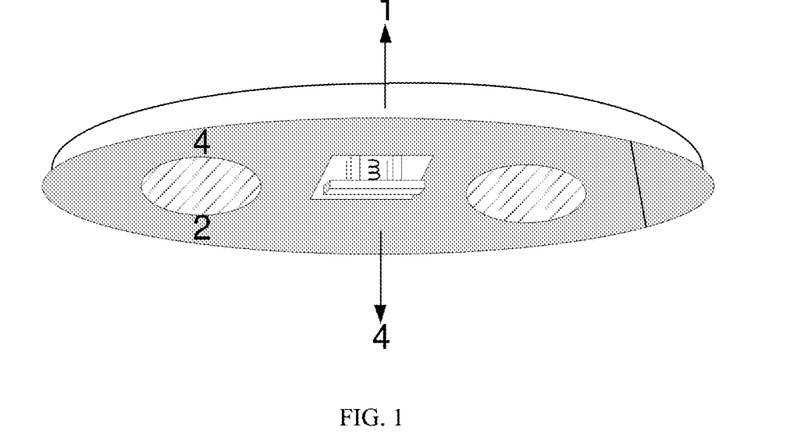
FIG. 1 is a schematic diagram of an overall structure of a chest non-invasive blood pressure detecting probe based on pulse wave transit time according to an embodiment of the disclosure.

As shown in FIG. 1, a chest non-invasive blood pressure detecting probe based on pulse wave transit time includes a probe body and a patch 4. Considering the convenience of replacement, the electrode sheets of the present disclosure are provided on the patch 4, and then attached and mounted, in a male-female fasteners form, on the probe body for use. So, when the patch needs to be replaced, the patch 4 can be directly removed and replaced with a new patch.

The probe body includes a shell 1 and a flexible bottom plate 2-4. The shell 1 is semi-elliptical, and the flexible bottom plate 2-4 is provided at the bottom of the shell 1 to close a lower open part of the shell 1. There is a cavity between the shell 1 and the flexible bottom plate 2-4. A circuit board, a power supply, a storage module and other components matched with the probe can be provided in the cavity according to the actual required functions. In order to adapt to the flexible deformation of the whole probe, the substrate for mounting the detection circuit therein, the shell 1 and the flexible bottom plate 2-4 need to be made of flexible materials.

Figure 2:
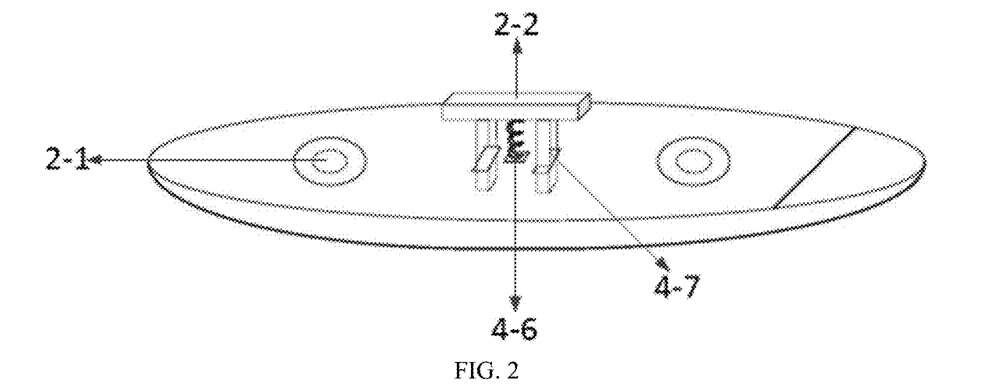
FIG. 2 is a schematic perspective diagram of a probe body according to an embodiment of the disclosure.
Figure 3:
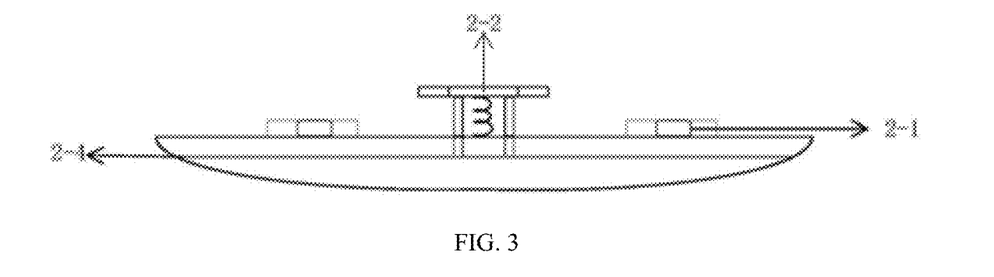
FIG. 3 is a side view of a probe body according to an embodiment of the disclosure.
Figure 4:
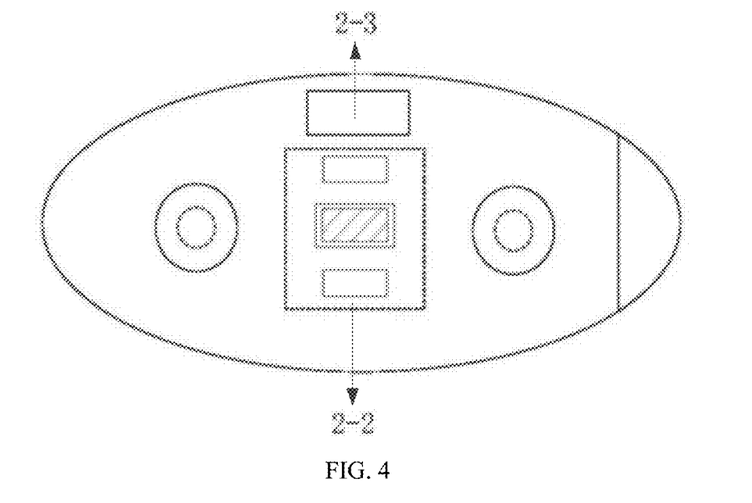
FIG. 4 is a schematic view of a surface arrangement (double electrodes) of a flexible bottom plate of a probe body according to an embodiment of the disclosure.

As shown in FIGS. 2-4, various detection elements are installed on the flexible bottom plate 2-4, and each detection element has its own installation form, which will be described in detail below. The surface of the flexible bottom plate 2-4 is provided with a plurality of electrode female fasteners 2-1, a photoelectric sensor module 2-2 and an acceleration sensor 2-3. In this embodiment, there are two electrode female fasteners 2-1 that are symmetrically provided on both sides of the photoelectric sensor module 2-2, which is in the form of double electrodes. The acceleration sensor 2-3 is provided at an upper side of the photoelectric sensor module 2-2. The electrode female fasteners 2-1 and the acceleration sensor 2-3 are attached closely on the surface of the flexible bottom plate 2-4. The photoelectric sensor module 2-2 is fixed on the elastic component. The elastic component includes two fixed telescopic rods 4-7 and a spring conductive wire 4-6. Two fixed telescopic rods 4-7 are vertically fixed at the bottom of the photoelectric sensor module 2-2, and the two fixed telescopic rods 4-7 are inserted into slotted holes formed on the flexible bottom plate 2-4. The two fixed telescopic rods 4-7 and the slotted holes form a moving pair capable of being telescopically adjusted up and down. The photoelectric sensor module 2-2 is always parallel to the surface of the flexible bottom plate 2-4 during the up and down movement. The spring conductive wire 4-6 is a spring-like conductive signal wire with elasticity. The bottom of the photoelectric sensor module 2-2 is connected with one end of the spring conductive wire 4-6, and the other end of the spring conductive wire 4-6 is supported on the flexible bottom plate 2-4. The photoelectric sensor module 2-2 protrudes from the surface of the flexible bottom plate 2-4 under the support of the spring conductive wire 4-6 without external pressure. When the photoelectric sensor module 2-2 is pressed, the spring conductive wire 4-6 moves to the flexible bottom plate 2-4, and the photoelectric sensor module 2-2 is attached closely to the skin. Therefore, the elastic component can ensure that the photoelectric sensor module 2-2 is in close contact with the skin during use, which improves the signal quality. The lower part of the spring conductive wire 4-6 can extend below the flexible bottom plate 2-4, and is connected with the detection circuit, so as to transmit the original data acquired by the photoelectric receiving tube PD. Similarly, the signal line of the acceleration sensor 2-3 also extends below the flexible bottom plate 2-4 and is connected with the detection circuit.

Figures 5A, 5B, 5C:
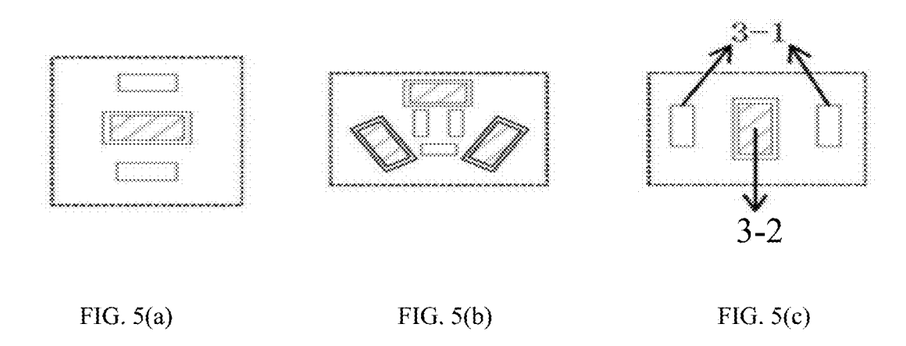
FIG. 5(a) is a schematic diagram of an arrangement of a photoelectric sensor module according to an embodiment of the disclosure.
FIG. 5(b) is another schematic diagram of an arrangement of a photoelectric sensor module according to an embodiment of the disclosure.
FIG. 5(c) is yet another schematic diagram of an arrangement of a photoelectric sensor module according to an embodiment of the disclosure.

The photoelectric sensor module 2-2 acquires human pulse and blood flow volume signals, and the photoelectric sensor module 2-2 can acquire and process data based on the photoplethysmographic method. The photoelectric sensor module 2-2 includes one or more photoelectric receiving tubes PD3-2 and one or more LED arrays 3-1. The photoelectric receiving tubes 3-2 are used for receiving light beams emitted by the LED array(s) 3-1 and then reflected by skin. The pulse signal PPG is acquired by the photoelectric sensor module 2-2. The light beam with a certain wavelength emitted by the LED array(s) 3-1 passes through the chest skin, and is received by the photoelectric receiving tube(s) 3-2 after being reflected by the skin. The photoelectric signal is converted into an electrical signal for output, thereby obtaining the fluctuation change of the arterial blood. There are many arranging methods of the LED arrays 3-1 and the photoelectric receiving tubes 3-2, among which three methods are listed in FIG. 5 (a)-FIG. 5(c), whereas the arranging method thereof can be selected as required in practical application. The LED array preferably includes three kinds of LEDs with wavelengths of 880 nm, 660 nm and 940 nm, and the specific wavelengths of the LEDs can also be adjusted as required.

Figure 6:
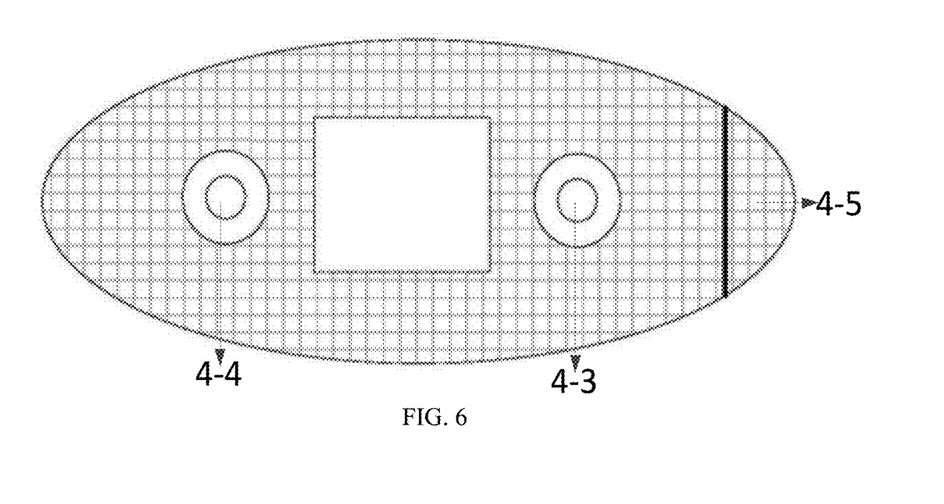
FIG. 6 is a schematic plan view of a patch according to an embodiment of the disclosure.
Figure 7:
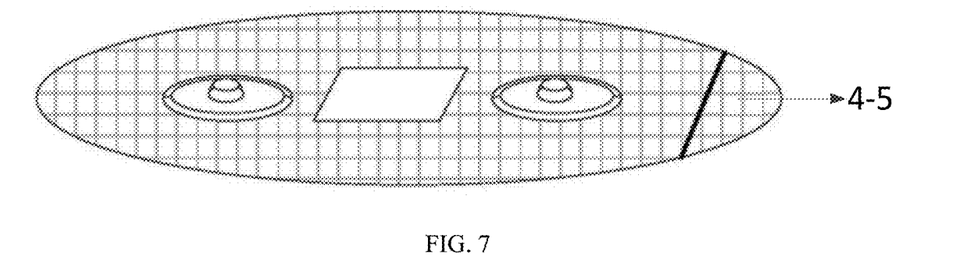
FIG. 7 is a schematic perspective view of a patch according to an embodiment of the disclosure.
Figure 8:
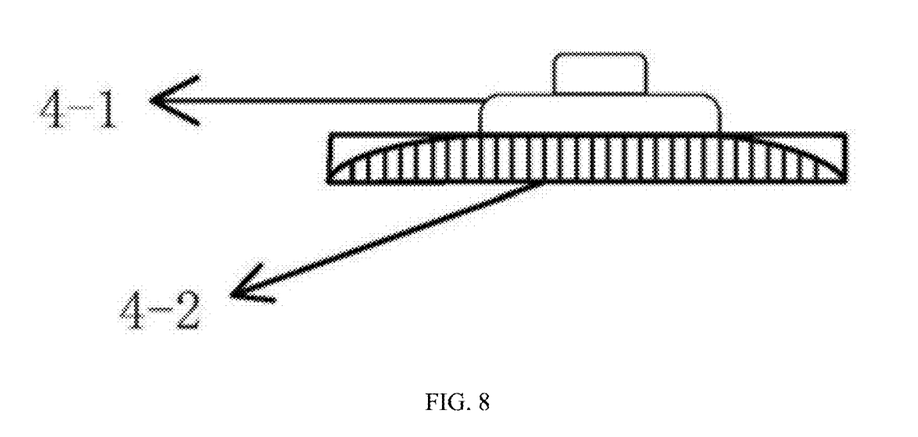
FIG. 8 is a structural schematic diagram of an electrode assembly according to an embodiment of the disclosure.

The probe body is used to integrate the electronic components required for detection, and serves as a mounting bracket for the patch 4. As shown in FIGS. 6 and 7, there are two electrode assemblies in the patch 4, and each electrode assembly includes an electrode sheet and an electrode male fastener 4-1. The external contour of the patch 4 is the same as that of the surface of the flexible bottom plate 2-4, and the middle thereof is formed with a hollow area. When the patch 4 is attached closely to the surface of the flexible bottom plate 2-4, the photoelectric sensor module 2-2 can extend out of the surface through the hollow area for easy contacting with the skin. The electrode male fasteners 4-1 of all electrode assemblies are embedded and fixed on the surface of the patch 4, and the electrode male fasteners and the electrode female fasteners 2-1 are arranged on the surface of the flexible bottom plate 2-4 in one-to-one correspondence. That is, when the patch 4 is attached closely to the surface of the flexible bottom plate 2-4, the electrode male fasteners 4-1 and the electrode female fasteners 2-1 can be snapped and fixed in pairs. The male and female fasteners are detachably fixed and can be removed and replaced at any time. As shown in FIG. 8, an electrode sheet is attached to a surface of each electrode male fastener 4-1, and the surface of the electrode sheet is coated with a gel layer 4-2, so as to ensure the stability of the detection source signal and the reliability of the contact. The electrode female fastener 2-1 and the electrode male fastener 4-1 have matching contacts for signal transmission, and the electrode female fasteners 2-1 are directly connected with the detection circuit inward. After the patch 4 is assembled with the probe body, the signals are acquired through the electrode sheets, and then enter the detection circuit through the male and female fasteners of the electrodes for subsequent signal processing. In addition, a reference electrode 4-5 is also provided at one side edge of the patch 4. The reference electrode 4-5 can be directly and closely attached to the patch, or the attachment of the reference electrode can be in the male-female fastener form. Electrode sheets that are above mentioned can be made of Ag/AgCl, metal or fabric electrodes.

The electrode assemblies are arranged in pairs, and two electrode assemblies form a pair. There are two forms that are double electrodes and four electrodes. In this embodiment, a double-electrode form is adopted. The two electrodes can be used to detect ECG and cardiac impedance signals. When detecting ECG signals, the first electrode 4-3 is an RA electrode and the second electrode 4-4 is an LA electrode. Meanwhile, The RA electrode and the LA electrode can cooperate with the reference electrode 4-5 to reduce common mode interference, thereby detecting the electrical signal ECG of a heart movement of the human. The RA and LA electrodes can be simultaneously used to detect the cardiac impedance signal ICG. When detecting the cardiac impedance signal, the first electrode 4-3 is the detection electrode and the second electrode 4-4 is the excitation electrode. The two electrodes are cooperated with each other to extract the impedance change signal of the aortic blood flow.

Figure 9:
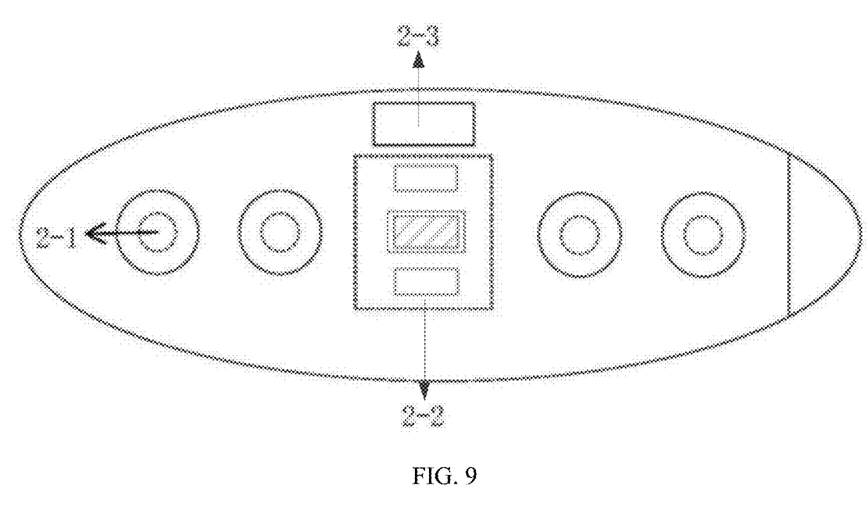
FIG. 9 is another schematic view of a surface arrangement (four electrodes) of a flexible bottom plate according to an embodiment of the disclosure.
Figure 10:
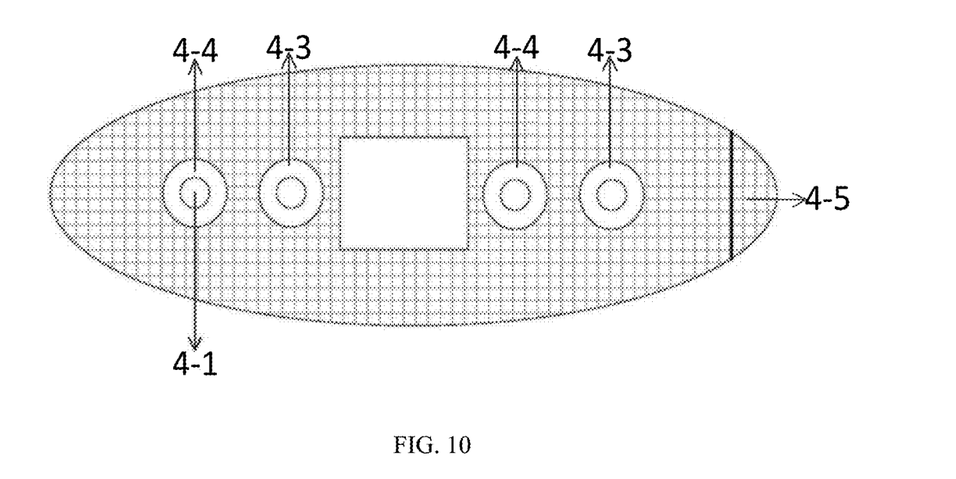
FIG. 10 is another schematic plan view (four electrodes) of a patch according to an embodiment of the disclosure.

However, in another embodiment, a four-electrode form may be used, and four electrodes are symmetrically distributed on both sides of the photoelectric sensor module 2-2 respectively. When the four-electrode form is used, the schematic plane view of the arrangement of the flexible bottom plate is shown in FIG. 9, and the schematic plane view of the patch needs to be adaptively adjusted as shown in FIG. 10. At this time, there are two pairs of electrode assemblies, namely, two first electrodes 4-3 and two second electrodes 4-4. When detecting ECG signals, first electrodes 4-3 are used as RA electrodes, and second electrodes 4-4 are used as LA electrodes. At the same time, four electrodes are simultaneously used for detecting cardiac impedance signal ICG. At this time, two first electrodes 4-3 are used as detection electrodes, and two second electrodes 4-4 are used as excitation electrodes. In addition, similarly, the reference electrode 4-5 can also be cooperated with the four electrodes to reduce the common mode interference.

In this embodiment, the shell 1 is made of flexible skin-friendly material, so that the probe can be deformed integrally and attached closely to the skin better. The shell 1 and the flexible bottom plate 2-4 can be both made of polydimethylsiloxane (PDMS).

In addition to electrodes and hollowed areas, the surface of the patch 4 can have an attached layer made of adhesive materials or formed by coating. So, the detecting probe and the device provided by the present disclosure can be attached closely to the skin surface of the human chest, thereby realizing the wearable function, which is free from the constraints of traditional blood pressure measurement airbags on the human body, and improves the comfort and the portability. The detecting probe is portable and used for continuous dynamic real-time acquiring of the aortic blood pressure of the human, which is free from the constraints of lead wires, has a small volume and higher comfort, higher measuring precision, and the higher medical value and the broader market application prospect.

The above chest non-invasive blood pressure detecting probe based on pulse wave transit time is used to obtain blood pressure-related detection signals, whereas its specific data processing needs to be matched with corresponding circuits to be realized. For convenience of understanding, based on the detecting probe, the present disclosure provides a chest non-invasive blood pressure detecting device based on pulse wave transit time.

In addition to the chest non-invasive blood pressure detecting probe, the detecting device further includes a signal processing system matched with the probe. The probe and signal processing system have the functions of signal acquiring, transmission and processing, and are wholly divided into an ECG/cardiac impedance signal detector, a pulse signal detector, an acceleration body plethysmography signal detector, a main control/Bluetooth unit, a power supply management unit and a storage unit according to the function.

Figure 12:
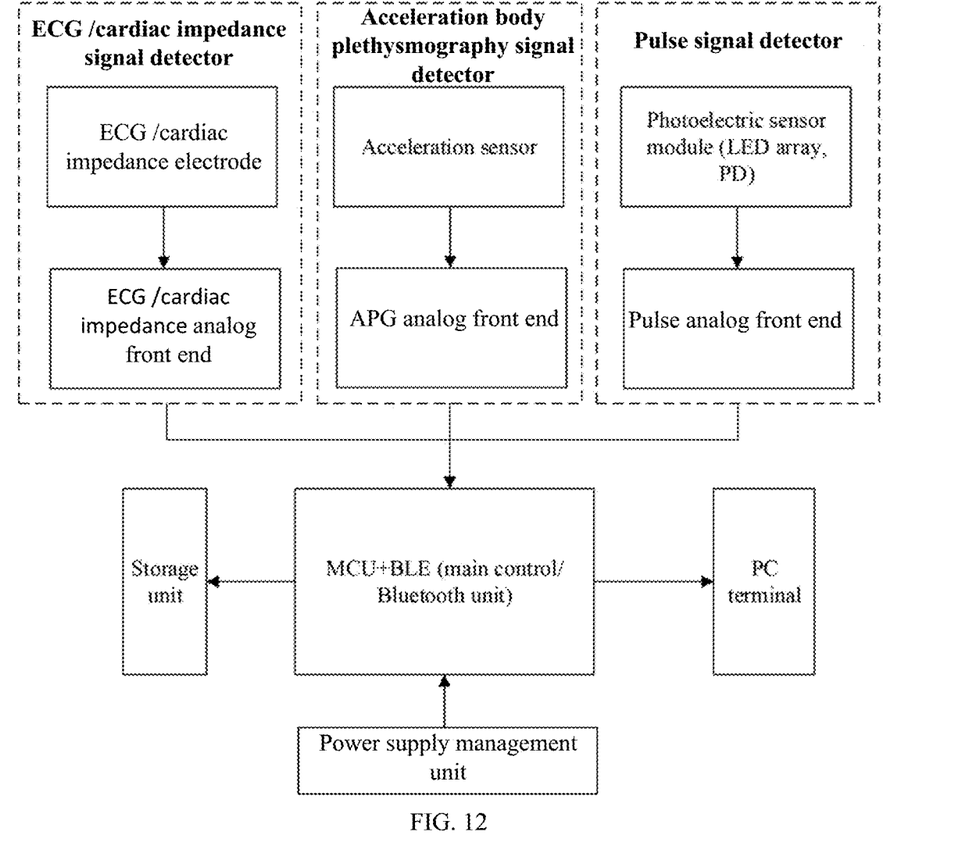
FIG. 12 is a schematic structural diagram of units of a chest non-invasive blood pressure detecting device based on pulse wave transit time according to an embodiment of the disclosure.
Figure 13:
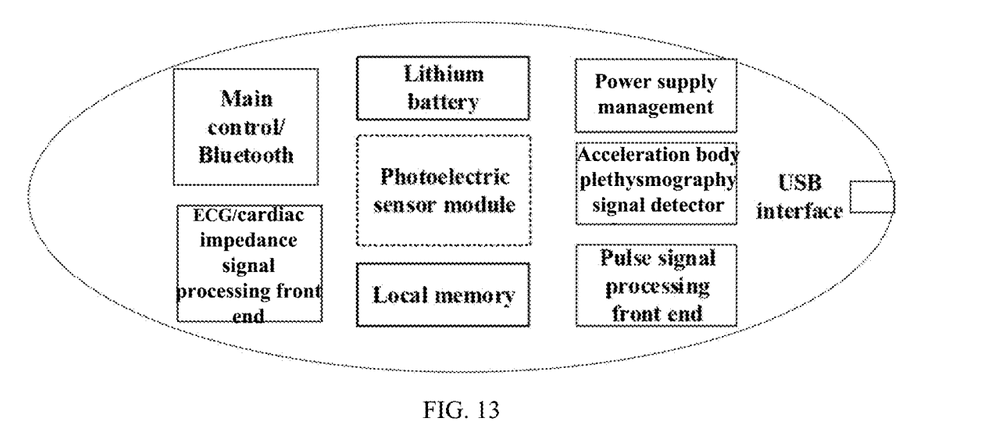
FIG. 13 is a schematic diagram of an arrangement of a signal processing system matched with a probe on the substrate according to an embodiment of the disclosure.

As shown in FIG. 12, the ECG/cardiac impedance signal detector includes an ECG signal analog front end and electrode assemblies on the patch 4. The electrode sheets on the electrode assemblies are used for picking up ECG signals and ICG signals of the human body surface. The ECG signal analog front end acquires ECG and ICG signals, and then processes and converts the signals. The pulse signal detector includes a photoelectric sensor module 2-2 and a pulse analog front end. The photoelectric sensor module 2-2 picks up human pulse and blood flow volume signals based on the photoplethysmographic method. The pulse analog front end processes and converts the signals. The acceleration body plethysmography signal detector includes an acceleration sensor 2-3 and an analog front end. The acceleration sensor 2-3 is used for acquiring the human artery acceleration body plethysmography APG signal, and the analog front end processes and converts this signal. The main control/Bluetooth unit includes a main control chip which contains Bluetooth BLE low power-protocol stack. The main control chip is configured to control the signal data acquisition of the signal detection units, such as the ECG/cardiac impedance signal detector, the pulse signal detector, the acceleration body plethysmography signal detector and so on; to receive, store, and analyze signals, extract features of the signals and calculate blood pressure; and then to send blood pressure detection results to the terminal through Bluetooth protocol stack. The power supply management unit is used to supply the electric power to the power consumption unit. The power supply management unit can include a lithium battery module, a voltage stabilizing circuit and a USB interface. The USB interface is used for externally connecting the power supply and charging the lithium battery module. The lithium battery module is used for internally supplying the electric power, and the voltage stabilizing circuit is used for converting the voltage and enabling the stable output of the voltage. The storage unit is used to store local data, and a MicroSD card can be used. FIG. 13 is a schematic diagram showing an arrangement of the signal processing system matched with the probe on the substrate.

Figure 11:
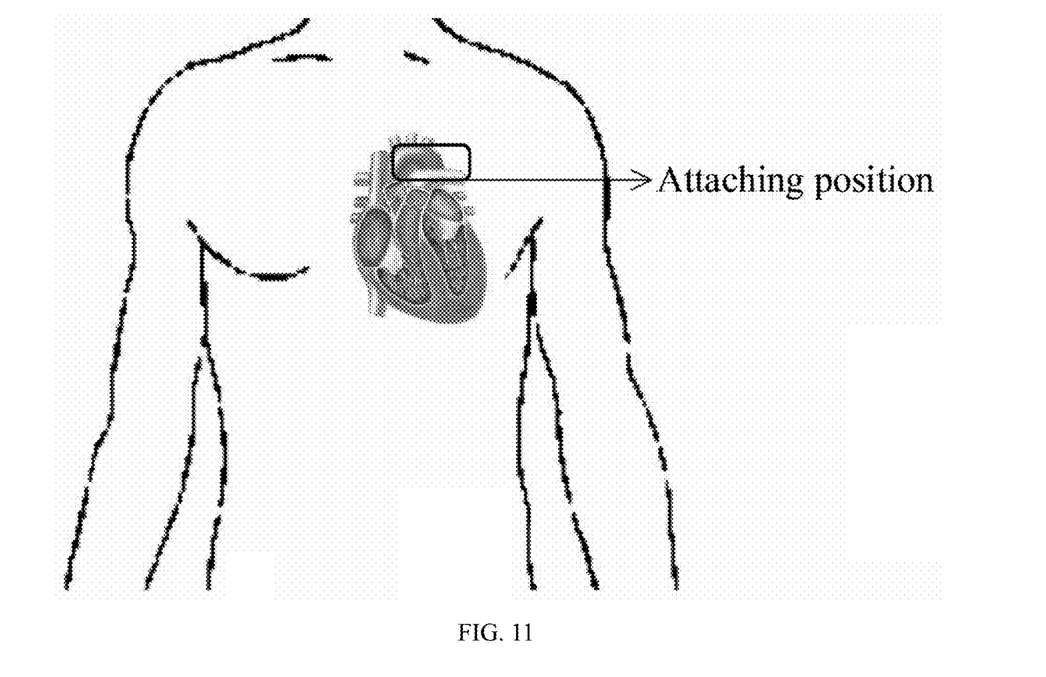
FIG. 11 is a schematic diagram of an attaching position of a chest non-invasive blood pressure detecting probe on a human body according to an embodiment of the disclosure.

The use process of the chest non-invasive blood pressure detecting device is as follows. The probe body and the patch are assembled by the male and female fasteners of electrodes, and the system is attached closely to the outlet of the aorta of the human chest (FIG. 11). The photoelectric sensor module 2-2 is attached closely to the skin under the action of elasticity, and starts to detect the blood pressure of the human aorta. After starting detection, the main control unit controls each signal detection unit to start acquiring signals. The ECG/cardiac impedance signal detector picks up ECG signals through RA and LA electrodes and the reference electrode 4-5, and picks up ICG signals through excitation electrodes and detection electrodes. ECG/ICG signals are transmitted to the main control unit after being acquired, converted and amplified by the ECG/cardiac impedance signal analog front end. The pulse signal detector acquires the human aortic PPG signal through the photoelectric sensor module 2-2, and this signal is amplified and converted by the pulse signal analog front end and thus sent to the main control chip in the main control/Bluetooth unit. The main control chip performs waveform processing and feature extraction on the summarized signals, calculates blood pressure according to the blood pressure calculation model, and sends the results to the terminal (mobile phone/PC) via Bluetooth.

In the process of signal detection, the RA and LA electrodes on the patch are located on both sides, and the reference electrode 4-5 is used to reduce common mode interference and detect ECG signals of the human heart movement. Electrodes can be simultaneously used to detect the cardiac impedance signal ICG: the constant current with high frequency and low amplitude is input by excitation electrodes; periodic changes of the blood flow of the thoracic cavity are caused by cardiac periodic activities, thereby causing periodic changes of thoracic resistance; and detection electrodes detect voltage signals induced by aortic blood flow, and impedance change signals ICG of aortic blood flow are extracted from voltage signals by a switch demodulator. The acceleration body plethysmography signal APG is acquired by a high-sensitivity acceleration sensor 2-3, which can reliably capture the displacement change of the artery wall towards the skin surface caused by the systole and the diastole. The pulse signal PPG is acquired by the photoelectric sensor module 2-2. The light beam with a certain wavelength emitted by the LED arrays 3-1 passes through the skin of the chest, and is received by the photoelectric receiving tubes 3-2 after being reflected by the skin. The photoelectric signal is converted into an electrical signal for output, thereby obtaining the fluctuation change of the arterial blood.

The analysis processing program in the main control unit can be set as required. For convenience of understanding, one of the methods for calculating blood pressure in the main control unit is given below. The specific calculation process is as follows.

1) After obtaining the detection data of the individual to be detected, the main control unit can extract the features of the original waveform signal. The detection data includes an ECG signal, a PPG signal, an ICG signal and an APG signal.
2) The pulse wave transit time PTT, the pre-ejection period PEP, the heart rate HR and the morphological parameter C of the normalized pulse wave are obtained by waveform characteristics. The conductance parameter of the skin is obtained by ICG signals, and represented by a formula $$\rho = \frac{1}{ICG}.$$

The calculation method of the pulse wave transit time PTT is that: extracting features of the ECG waveform signal and the PPG waveform signal, storing the time record $t_R$ of the peak R of the ECG signal and the trough time record $t_P$ of the PPG signal, and calculating the pulse wave transit time by a formula $PTT=T_P-T_R$.

The calculation method of the pre-ejection period PEP is that: extracting the features of the ECG waveform signal and the APG waveform signal, storing time record $t_Q$ of the peak Q of the ECG signal and the time record $t_A$ of the peak of the APG signal, and calculating the pre-ejection period by a formula $PEP=T_A-T_Q$.

The morphological parameter C of the pulse wave includes AIx, SIx, RT, DT, K, PA, PHH, Pmax, Pmin, Ppeak, etc. In order to simplify the regression model and prevent over-fitting, that statistics on the Pearson correlation coefficient is realized by univariate and multivariate regression analysis. In the present disclosure, only a few morphological parameters with higher correlation are selected: SIx, RT, DT, K. Therefore, in the present disclosure, the morphological parameter of the pulse wave is determined by a formula C=[SIx RT DT K] (where SIx is a hardening index, RT is rising time, DT is falling time, K is pressure constant).

3) The pulse wave transit time PTT', which is after removing the pre-ejection period, is calculated by a formula PTT'=PTT−PEP.

4) According to the blood pressure model represented by a formula $$BP = \alpha * \frac{1}{PTT'^2} + \beta * HR + \gamma C + \lambda \rho,$$

the PTT' value, the HR value, the C value and the ρ value of the individual to be detected are substituted into this formula to obtain the blood pressure value BP.

Parameters α, β, γ and λ, in the above blood pressure model are all weights, and the specific values thereof can be calibrated and fitted by using calibration data containing accurate blood pressure values in advance, so as to obtain corresponding fitting parameters.

This blood pressure model is improved on the traditional blood pressure model based on pulse wave transit time. Considering the pre-ejection period and other factors affecting blood pressure changes, the parameters such as heart rate, pulse wave morphology parameters and skin conductance are added to modify the blood pressure model, which can ensure that more accurate blood pressure values can be obtained within a longer calibration interval. With this method, the systolic blood pressure SBP and the diastolic blood pressure DBP can be obtained by calibration. In order to prove the effect of the method of the present disclosure, multiple groups of data of a single sample are selected for error analysis and compared with two classical models. The error analysis of the average values and the variances of the systolic blood pressure and the diastolic blood pressure are shown in Table 1 below, which shows that the precision of the blood pressure calculation method of the present disclosure is obviously improved.

TABLE 1

| Model category | Average value of SBP | Variance of SBP | Average value of DBP | Variance of DBP |
|---|---|---|---|---|
| Classical model 1 | −0.0137 | 5.5834 | −0.0069 | 2.4124 |
| Classical model 2 | −0.0049 | 5.2186 | −0.0194 | 1.9884 |
| Model of this method | −0.0046 | 4.0378 | −0.0045 | 1.8884 |

It should be noted that in the chest non-invasive blood pressure detecting device, circuits, modules or units are necessary, whereas they are not necessary for the detecting probe itself and can be adjusted as needed. The detecting probe of the present disclosure is mainly a front-end data acquiring assembly, which aims to provide a probe structure capable of acquiring different related parameters of the blood pressure. However, the specific back-end processing circuits, modules, units and so on can be adjusted according to actual needs, and the blood pressure calculation algorithm can also adopt the corresponding model in the prior art, which are not limited.

Compared with that prior art, the technical scheme provided by the present disclosure has the follow advantages.

1) As a wearable signal acquiring system, the chest non-invasive blood pressure detecting probe of the present disclosure can be attached closely to the skin surface of the human chest, and includes a probe body and a patch, which are of spilt type. The patch is attached and mounted, in a male-female fastener form, on the probe body for use, so that when the patch needs to be replaced, the patch can be directly removed and replaced with a new patch, which is convenient for use.

2) Considering that the pulse wave transit time PTT in the traditional detection method ignores the time parameter in the pre-ejection period, in the disclosure, the measurement position is fixed at the outlet of the thoracic aorta, the pre-ejection period PEP in the cardiac ejection period is obtained through an ECG signal and an aortic acceleration body plethysmography signal APG, and that the influence of the pre-ejection period PEP on the pulse wave transit time PTT is removed, thereby obtaining a more accurate pulse wave transit time PTT'. In this way, the detected transit time is closer to the actual transit time, and the accurate aortic blood pressure can be guaranteed.

3) Considering the defect of unsatisfactory precision of the traditional non-invasive blood pressure detection, in the present disclosure, the blood pressure model is improved by adding the heart rate HR, the morphological parameter C of the pulse wave and the skin conductance p, so that the model fitting result is more accurate.

4) According to the principle of PTT non-invasive continuous blood pressure measurement, the signal acquiring system is integrated into the chest wearable device, and the chest I-lead ECG, the cardiac impedance plethysmography, the aortic volume pulse wave graph and the aortic acceleration body plethysmography can be synchronously acquired during detection. The measuring apparatus is simple in structure, convenient to operate, and free from the constraints of traditional blood pressure measurement airbags on the human body, and has improved comfort and portability. The detecting probe is portable and used for continuous dynamic real-time acquiring of the human aortic blood pressure, free from the constraints of lead wires, is small and comfortable, is high in measuring precision, as well as has higher medical value and broader market application prospects.

In this specification, each embodiment is described in a progressive manner, and each embodiment focuses on the differences from other embodiments. It is sufficient to refer to the same and similar parts among various embodiments.

In the present disclosure, a specific example is applied to illustrate the principle and implementation of the present disclosure, and the explanation of the above embodiments is only used to help understand the method and its core idea of the present disclosure. At the same time, according to the idea of the present disclosure, there will be some changes in the specific implementation and application scope for those skilled in the art. To sum up, the contents of this specification should not be construed as limiting the present disclosure.

What is claimed is:

1. A chest non-invasive blood pressure detecting probe based on pulse wave transit time, the detecting probe comprising a shell, a patch and an elastic component; wherein
a bottom of the shell is provided with a flexible bottom plate, and a surface of the flexible bottom plate is provided with a plurality of electrode female fasteners, a photoelectric sensor module and an acceleration sensor;
the electrode female fasteners and the acceleration sensor are closely attached on the surface of the flexible bottom plate; the photoelectric sensor module is fixed on the elastic component;
the elastic component comprises two fixed telescopic rod and a spring conductive wire;

the two fixed telescopic rods are fixed at a bottom of the photoelectric sensor module; the flexible bottom plate is provided with slotted holes; the two fixed telescopic rods are inserted into the slotted holes to form a movable pair capable of telescopic adjustment; the bottom of the photoelectric sensor module is connected with one end of the spring conductive wire, and another end of the spring conductive wire is supported on the flexible bottom plate; the photoelectric sensor module protrude from the surface of the flexible bottom plate without external pressure;

a plurality of electrode assemblies are provided in the patch; the electrode assemblies comprise respective electrode sheets and respective electrode male fasteners;

the patch has a same external contour as the surface of the flexible bottom plate, and a middle portion of the patch is provided with a hollow area; the photoelectric sensor module is placed in the hollow area, and the photoelectric sensor module is connected with the flexible bottom plate through the two fixed telescopic rods inserted into the slotted holes; the electrode male fasteners of the electrode assemblies are fixedly embedded on a surface of the patch, the electrode male fasteners and the electrode female fasteners are arranged in one-to-one correspondence, and the electrode male fasteners and the electrode female fasteners are snapped and fixed in pairs; a surface of each of the electrode male fasteners is closely attached with a corresponding one of the electrode sheets.

2. The chest non-invasive blood pressure detecting probe based on pulse wave transit time according to claim 1, wherein the electrode assemblies are arranged in pairs, the electrode assemblies comprise two setting manners that are double electrodes and four electrodes; each pair of the electrode assemblies is symmetrically arranged with the photoelectric sensor module as a center.

3. The chest non-invasive blood pressure detecting probe based on pulse wave transit time according to claim 2, wherein a reference electrode is provided on the patch.

4. The chest non-invasive blood pressure detecting probe based on pulse wave transit time according to claim 1, wherein the electrode sheets are made of Ag/AgCl, metal or fabric electrodes; a gel layer is coated on a surface of each of the electrode sheets.

5. The chest non-invasive blood pressure detecting probe based on pulse wave transit time according to claim 1, wherein the photoelectric sensor module comprises at least one photoelectric receiving tube and at least one LED array; the at least one photoelectric receiving tube is used for receiving light beams emitted by the at least one LED array and reflected by human skin.

6. The chest non-invasive blood pressure detecting probe based on pulse wave transit time according to claim 1, wherein a cavity for accommodating a detection circuit is provided between the shell and the flexible bottom plate.

7. The chest non-invasive blood pressure detecting probe based on pulse wave transit time according to claim 1, wherein the shell and/or the flexible bottom plate are made of polydimethylsiloxane.

8. A chest non-invasive blood pressure detecting device based on pulse wave transit time, the chest non-invasive blood pressure detecting device comprising the chest non-invasive blood pressure detecting probe based on pulse wave transit time, the chest non-invasive blood pressure detecting probe comprising a shell, a patch and an elastic component; wherein a bottom of the shell is provided with a flexible bottom plate, and a surface of the flexible bottom plate is provided with a plurality of electrode female fasteners, a photoelectric sensor module and an acceleration sensor;

the electrode female fasteners and the acceleration sensor are closely attached on the surface of the flexible bottom plate; the photoelectric sensor module is fixed on the elastic component;

the elastic component comprises two fixed telescopic rod and a spring conductive wire;

the two fixed telescopic rods are fixed at a bottom of the photoelectric sensor module; the flexible bottom plate is provided with slotted holes; the two fixed telescopic rods are inserted into the slotted holes to form a movable pair capable of telescopic adjustment; the bottom of the photoelectric sensor module is connected with one end of the spring conductive wire, and another end of the spring conductive wire is supported on the flexible bottom plate; the photoelectric sensor module protrudes from the surface of the flexible bottom plate without external pressure;

a plurality of electrode assemblies are provided in the patch; the electrode assemblies comprise respective electrode sheets and respective electrode male fasteners;

the patch has a same external contour as the surface of the flexible bottom plate, and a middle portion of the patch is provided with a hollow area; the photoelectric sensor module is placed in the hollow area, and the photoelectric sensor module is connected with the flexible bottom plate through the two fixed telescopic rods inserted into the slotted holes; the electrode male fasteners of the electrode assemblies are fixedly embedded on a surface of the patch, the electrode male fasteners and the electrode female fasteners are arranged in one-to-one correspondence, and the electrode male fasteners and the electrode female fasteners are snapped and fixed in pairs; a surface of each of the electrode male fasteners is closely attached with a corresponding one of the electrode sheets;

wherein the detecting device further comprises an ECG/cardiac impedance (ICG) signal detector, a pulse signal detector, an acceleration body plethysmography signal detector, a main control/Bluetooth unit, a power supply management unit and a storage unit;

the ECG/cardiac impedance signal detector comprises an ECG signal analog front end and the electrode assemblies arranged in pairs; the electrode assemblies are electrically connected with the ECG signal analog front end;

the electrode sheets on the electrode assemblies are used for picking up ECG signals and ICG signals of a human body surface; the ECG signals and the ICG signals are processed and converted by the ECG signal analog front end;

the pulse signal detector comprises a pulse analog front end and the photoelectric sensor module; the photoelectric sensor module is electrically connected with the pulse analog front end;

the photoelectric sensor module is configured for picking up human pulse and blood flow volume signals based on a photoplethysmographic method, and the human pulse and blood flow volume signals are processed and converted by the pulse analog front end;

the acceleration body plethysmography signal detector comprises an acceleration photoplethysmography (APG) analog front end and the acceleration sensor; the acceleration sensor is electrically connected with the APG analog front end;

the acceleration sensor is used for acquiring APG signals; the APG signals are processed and converted by the APG analog front end;

the main control/Bluetooth unit comprises a main control chip; the main control chip comprises a Bluetooth Bluetooth low energy (BLE) low power-consumption protocol stack, which is electrically connected with the ECG/cardiac impedance signal detector, the pulse signal detector, the acceleration body plethysmography signal detector, the power supply management unit and the storage unit, respectively;

the main control chip is used for controlling each signal detection unit to acquire signal data, and performing signal processing on the signal data to obtain a blood pressure result; the signal processing comprises signal analysis, feature extraction and blood pressure calculation;

the blood pressure result is transmitted to a terminal via the Bluetooth BLE low power-consumption protocol stack;

the power supply management unit is used for providing electric energy for each power consumption unit in the detecting device;

the storage unit is used for storing local data;

the ECG signal analog front end, the pulse analog front end, the APG analog front end, the main control/Bluetooth unit, the power supply management unit and the storage unit are integrated in the detecting probe.

9. The chest non-invasive blood pressure detecting device based on pulse wave transit time according to claim 8, wherein when the electrode assemblies arranged in pairs are used for detecting the ECG signals, one of the electrode assemblies serves as a right atrial (RA) electrode, and another one of the electrode assemblies serves as a left atrial (LA) electrode; when the electrode assemblies arranged in pairs are used for detecting cardiac impedance signals, one of the electrode assemblies serves as a detection electrode, and another one of the electrode assemblies serves as an excitation electrode.

10. The chest non-invasive blood pressure detecting device based on pulse wave transit time according to claim 9, wherein a reference electrode is provided on the patch.

11. The chest non-invasive blood pressure detecting device based on pulse wave transit time according to claim 8, wherein the power supply management unit comprises a lithium battery module, a voltage stabilizing circuit and a USB interface;

the USB interface is used for externally connecting power supply; the lithium battery module is used for internally supplying electric power; and the voltage stabilizing circuit is used for converting a voltage and enabling stable output of the voltage.

12. The chest non-invasive blood pressure detecting device based on pulse wave transit time according to claim 8, wherein the electrode assemblies are arranged in pairs, the electrode assemblies comprise two setting manners that are double electrodes and four electrodes; each pair of the electrode assemblies is symmetrically arranged with the photoelectric sensor module as a center.

13. The chest non-invasive blood pressure detecting device based on pulse wave transit time according to claim 8, the electrode sheets are made of Ag/AgCl, metal or fabric electrodes; a gel layer is coated on a surface of each of the electrode sheets.

14. The chest non-invasive blood pressure detecting device based on pulse wave transit time according to claim 8, wherein the photoelectric sensor module comprises at least one photoelectric receiving tube and at least one LED array; the at least one photoelectric receiving tube is used for receiving light beams emitted by the at least one LED array and reflected by human skin.

15. The chest non-invasive blood pressure detecting device based on pulse wave transit time according to claim 8, wherein a cavity for accommodating a detection circuit is provided between the shell and the flexible bottom plate.

16. The chest non-invasive blood pressure detecting device based on pulse wave transit time according to claim 8, wherein the shell and/or the flexible bottom plate are made of polydimethylsiloxane.

* * * * *